United States Patent [19]
Walinsky

[11] Patent Number: 5,108,370
[45] Date of Patent: Apr. 28, 1992

[54] PERFUSION BALLOON CATHETER

[76] Inventor: Paul Walinsky, 220 E. Mermaid La., Townhouse #218, Philadelphia, Pa. 19118

[21] Appl. No.: 416,709

[22] Filed: Oct. 3, 1989

[51] Int. Cl.$^5$ .......................................... A61M 29/00
[52] U.S. Cl. ...................................... 604/96; 606/194
[58] Field of Search ............................. 604/96–104; 606/192, 194

[56] References Cited

U.S. PATENT DOCUMENTS

| | | | |
|---|---|---|---|
| 4,183,102 | 1/1980 | Guiset | 604/101 |
| 4,328,056 | 5/1982 | Snooks | 604/96 |
| 4,449,972 | 5/1984 | Krüger | 604/96 |
| 4,581,017 | 4/1986 | Sahota | 604/101 |
| 4,641,649 | 2/1987 | Walinsky et al. | |
| 4,641,653 | 2/1987 | Rockey | 604/96 |
| 4,643,186 | 2/1987 | Rosen et al. | |
| 4,762,129 | 8/1988 | Bonzel | 604/96 |
| 4,787,388 | 11/1988 | Hofmann | 606/194 |
| 4,909,252 | 3/1990 | Goldberger | 606/194 |
| 4,944,745 | 7/1990 | Sogard et al. | 606/194 |

OTHER PUBLICATIONS

Article entitled "Effect of Inflation Pressures on Coronary Angioplasty Balloons", by Jain et al., published at pp. 26–28 of the Jan. 1, 1986, issue of The American Journal of Cardiology.

"The Balloon on a Wire Device", by Myler et al., published at pp. 135–140 of vol. 14, No. 2, 1988 of Catheterization and Cardiovascular Diagnosis, published by Alan R. Liss, Inc., New York.

"Selection of Dilatation Hardware for PTCA-1985" by Topol et al., published at pp. 629–637 of vol. 11, No. 6, 1985 issue of Catheterization and Cardiovascular Diagnosis, published by Alan R. Liss, Inc., New York.

"Perfusion During Coronary Angioplasty", by Rossen, published at pp. 103–106 of the Jun. 1989 issue of the periodical Cardio.

*Primary Examiner*—C. Fred Rosenbaum
*Assistant Examiner*—William W. Lewis
*Attorney, Agent, or Firm*—William H. Meise

[57] ABSTRACT

A perfusion balloon catheter, as for angioplasty, has the balloon formed so that, when inflated within a vas or coronary artery, one or more channels are provided for the flow of bodily fluids or blood past the inflated balloon. In one embodiment, the balloon has a toroidal shape which defines a central open channel. In another embodiment, the balloon defines a multiply-lobed form which allows flow between the lobes. Balloon catheters with open channels, when used for angioplasty, reduce the likelihood of early termination of the procedure due to chest pain.

6 Claims, 9 Drawing Sheets

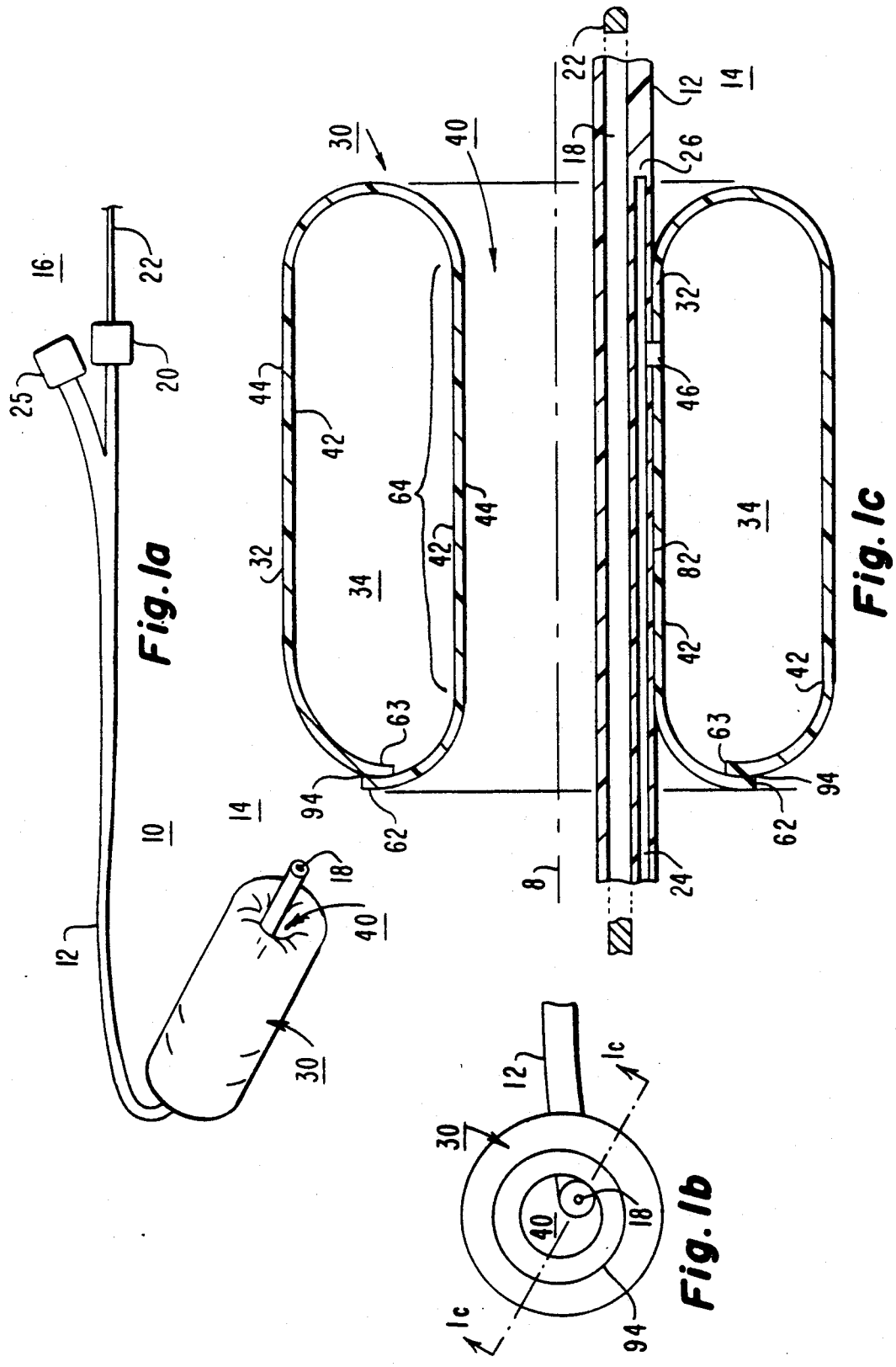

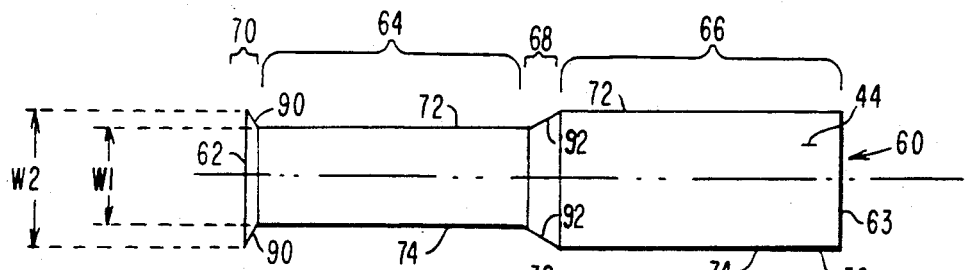
Fig.2a
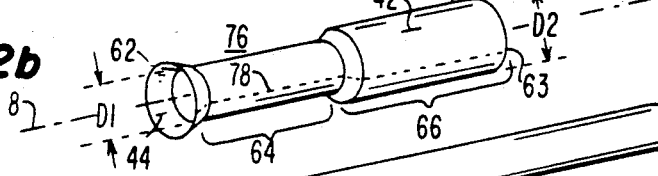
Fig.2b
Fig.2c
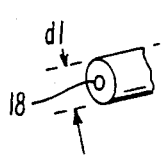
Fig.2d
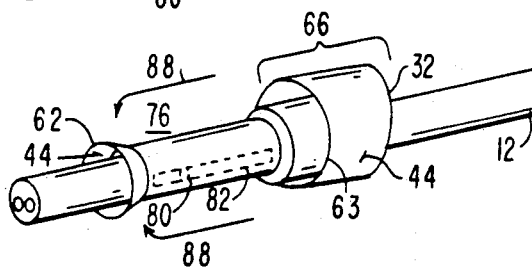
Fig.2e
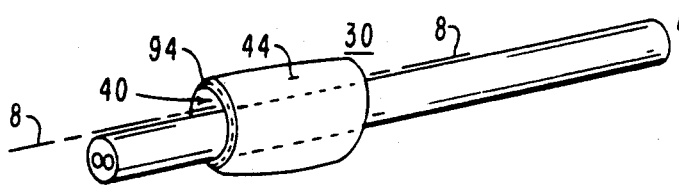
Fig.2f
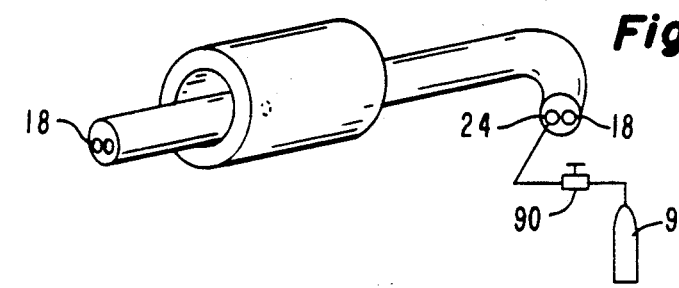
Fig.2g

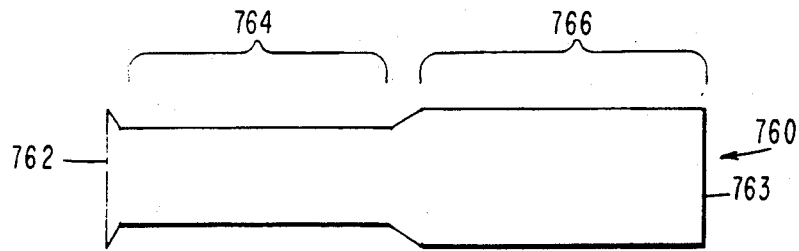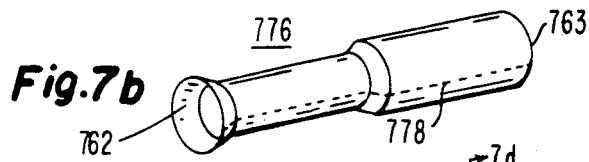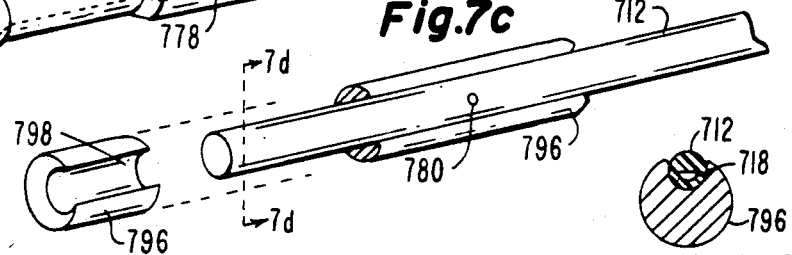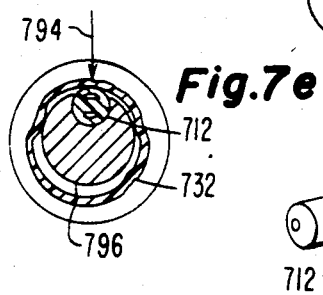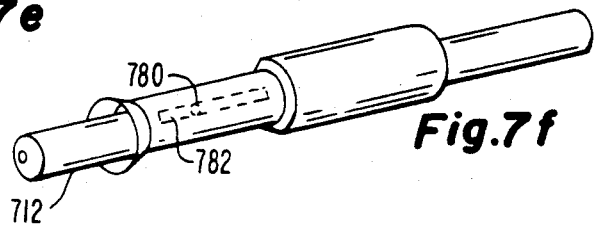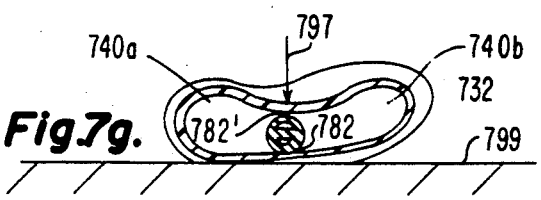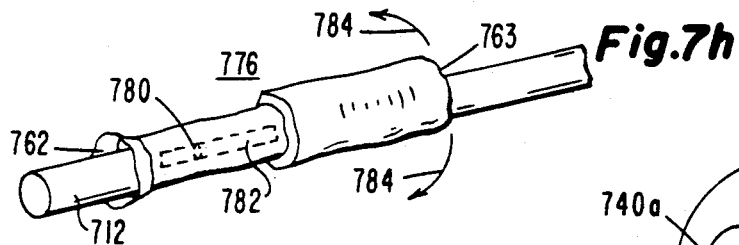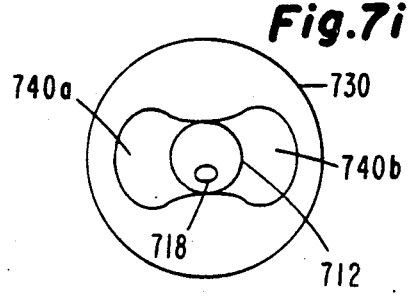

PERFUSION BALLOON CATHETER

BACKGROUND OF THE INVENTION

This invention relates to percutaneous transluminal coronary angioplasty (PTCA), and more particularly to angioplasty using balloon catheters in which the balloon allows perfusion in its inflated condition.

Coronary angioplasty is a widely used alternative to open-heart coronary bypass surgery for the treatment of acute and chronic heart problems. A major contributing factor in such heart problems is a reduction in nutrient blood flow to the muscles of the heart resulting from a reduction of blood flow through the coronary blood vessels. The reduction in flow may be caused by deposits of atherosclerotic plaque on the walls of the affected blood vessel, which causes a narrowing of the lumen or channel of the blood vessel. When the lumen is sufficiently narrowed, the rate of blood flow therethrough may be so diminished that spontaneous formation of a thrombus or clot occurs by a variety of physiologic mechanisms. Once a blood clot has begun to form, it extends within minutes into the surrounding blood, as mentioned in U.S. Pat. No. 4,643,186, issued Feb. 17, 1987, in the names of Rosen and Walinsky. The presence of atherosclerotic plaque not only reduces the blood flow to the muscles of the heart but is a major predisposing factor in coronary thrombosis.

The art relating to angioplasty includes many advances, such as the microwave-aided angioplasty described in the above-mentioned Rosen and Walinsky patent, reduced diameters as described in an article entitled "The Balloon On A Wire Device" by Myler et al, published at pages 135-140 of Volume 14, No. 2, 1988 of the periodical "Catheterization and Cardiovascular Diagnosis," published by Alan R. Liss, and various configurations of guide wires and catheter lumens, described for example in "Selection or Dilatation Hardware for PCTA-1985" by Topol et al., published at pages 629-637 of Volume 11, No. 6, 1985 of the aforementioned periodical.

In general, an angioplasty procedure is performed by obtaining access to the interior of the affected coronary artery, and advancing a deflated balloon to the location of the stenosis. The balloon is inflated by applying fluid pressure through an inflation/deflation ("inflation") lumen of the catheter, to thereby apply balloon pressure tending to expand the lumen of the coronary artery. When the stenotic portion of the lumen of the blood vessel or coronary artery has about the same diameter as adjacent portions which are free from plaque, the procedure may be terminated, the balloon deflated and the catheter removed. It has been observed, as in the article entitled "Perfusion During Coronary Angioplasty," by Rossen, published at pages 103-106 in the June 1989 issue of Cardio, that increased time with the balloon inflated is associated with an improved result.

Those portions of the heart muscle supplied with blood flow through the artery are partially deprived of blood flow when the catheter with deflated balloon is being positioned in the stenotic region, and may be completely deprived of blood flow when the balloon is inflated. This in turn has a tendency to decrease heart pumping efficiency, and the blood pressure tends to drop. Chest pains result in some patients. Either of these indications may undesirably require early termination of the procedure. Dilatation catheters are available, as mentioned in the above-mentioned Rossen article, in which perfusion or blood flow past the occluding catheter and balloon is provided by fenestrations or apertures into the distal lumen of the catheter on both sides of the balloon. When the distal lumen is also used for a guide wire, the guide wire must be retracted during perfusion, which requires additional manipulation, and may result in loss of position of the balloon. Further manipulation is required if the guide catheter surrounding the dilatation catheter must also be retracted. Such perfusion catheters tend to be somewhat larger in diameter and stiffer than conventional catheters having the same inflated balloon diameter, and are therefore more difficult to position. Also, their larger diameter excludes their use in the small arteries into which conventional balloon catheters may fit. It should also be noted that similar perfusion catheters without balloons may be used as a temporary or emergency measure until corrective surgery can be performed in cases of total occlusion.

SUMMARY OF THE INVENTION

A balloon catheter according to the invention is configured in such a manner that body fluids may continue to flow past the region undergoing treatment. In one embodiment of the invention, the balloon has an inflated shape which is roughly toroidal, i.e. including a longitudinal central aperture. In another embodiment of the invention, the inflated balloon includes one or more longitudinal lobes which, together with the surrounding walls of the vas or blood vessel, define at least one longitudinal channel for the flow of body fluids.

DESCRIPTION OF THE DRAWING

FIG. 1a is a perspective or isometric view of a dilatation catheter with toroidal inflated balloon, FIG. 1b is an axial or end view of the inflated balloon, showing the central channel, and FIG. 1c is a cross-section taken through the catheter, showing the balloon attachment region, FIGS. 1a, 1b and 1c are referred together as FIG. 1;

FIGS. 2a-2g, referred to jointly as FIG. 2, illustrate steps in the fabrication of the toroidal balloon catheter of FIG. 1;

FIGS. 5a-5d are together referred to as FIG. 5;

FIGS. 7a-7i, referred to jointly as FIG. 7, illustrate steps in making a balloon catheter with two perfusion channels;

DESCRIPTION OF THE INVENTION

Figure 3:
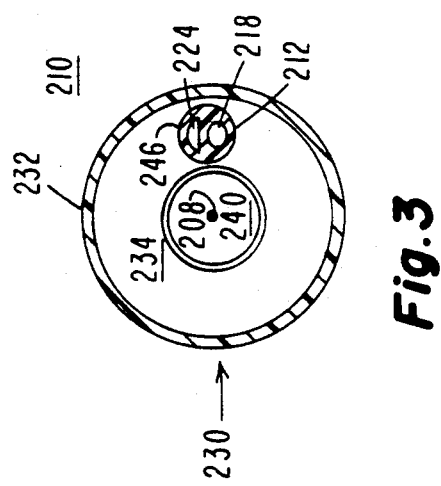
FIG. 3 is a cross-sectional axial view of a balloon catheter according to the invention in which the catheter passes through the balloon.

FIGS. 1a, 1b and 1c illustrate an angioplasty dilatation catheter according to the invention. In FIG. 1a, a catheter designated generally as 10 includes an elongated portion 12 and a balloon 30. Elongated portion 12 includes a distal end 14 and a bifurcated proximal end 16. Elongated portion 12 also includes a distal lumen 18 which extends from an open end at distal end 14 to an access aperture 20 at proximal end 16. Distal lumen 18 is dimensioned to provide a sliding fit for a guide wire, illustrated as 22. Such guide wires at the current state of the art have diameters of about 0.016 inches. The distal end of guide wire 22 may be positioned to extend beyond distal end 14 of elongated portion 12, as illustrated in FIG. 1c.

Also extending within elongated portion 12 of catheter 10 is a balloon inflation/deflation ("inflation") lumen 24, seen in cross-section in FIG. 1c. Balloon inflation lumen 24 extends from an access aperture 25 and within elongated portion 12 to terminate at a location 26, removed from the most distal end of elongated portion 12 but at or beyond balloon 30.

Balloon 30 includes a membrane 32. As illustrated in FIG. 1, balloon 30 when inflated has a shape which is generally toroidal. A toroid is a 3-dimensional shape formed by the revolution of a plane figure around an axis. In the case of balloon 30, the inflated portion 34 surrounded by membrane 32 as seen in cross-section is the plane figure, which is revolved about a central axis 8. More specifically, in FIG. 1c, the plane figure is the region lying above axis 8, designated 34 and bounded by membrane 32. Such a 3-dimensional shape is generally termed a "solid" of revolution, and this designation will be used herein, even though the "solid" portion is actually a hollow balloon.

It should be noted that the shapes of the balloon described herein occur only when the balloon is inflated. When the balloon is deflated, membrane 32 may be wrapped or closely formed about elongated portion 12 of catheter 10. The solid of revolution bounded by membrane 32 defines a central open channel 40. Central channel 40 allows body fluids to flow therethrough. Channel 40 extends through balloon 30 in the sense that body fluids may move axially parallel to catheter 10, but it is helpful to note that the toroidal shape of balloon membrane 32 defines a closed solid figure in which inflated region 34 is bounded by an inner surface 42, while channel 40 through which body fluids may flow is adjacent an exterior surface 44 of membrane 32. Thus, channel 40 does not extend through balloon 30 in the sense that fluids within the balloon co-mingle with body fluids. The use of the term "through the balloon" should be understood in this context.

The exterior diameter of elongated portion 12 of catheter 10 is smaller than the interior diameter of channel 40. The exterior surface of elongated portion 12 is attached to balloon 30 along one side of channel 40, which as illustrated in FIG. 1c is the lower side of channel 40. An inflation/deflation ("inflation") aperture 46 extends through membrane 32 at the point of attachment to provide communication between inflation lumen 24 and balloon interior 34.

FIG. 2 illustrates steps of a method for making the catheter of FIG. 1. Elements of FIG. 2 corresponding to those of FIG. 1 are designated by the same reference numeral. FIG. 2a illustrates side 44 of a plane sheet 60 of balloon membrane material. The opposite side (not visible in FIG. 2a) is side 42. As described below, a suitable material is polyethylene terephthalate. Sheet 60 includes a proximal end 62, an opposite end 63, a portion 64 which will be the portion adjacent channel 40, and another portion 66 which will define the outermost portion of the balloon. Portion 64 has a width W1 which is less than the width W2 of portion 66. A connecting portion 68 with sides 92 tapers in width between portions 64 and 66. A generally similar portion 70 with sides 90 adjoins portion 64.

Planar sheet 60 defines an upper edge 72 and a lower edge 74, both of which extend between proximal end 62 and opposite end 63. Sheet 60 is rolled into cylindrical form or tube 76, and edges 72 and 74 are joined along a seam 78, as illustrated in FIG. 2b. The term "cylindrical" is used in its conventional sense of a line (such as edge 72) rotated about an axis (such as axis 8). Tube 76 has diameters which vary along its length. Diameter D1 of portion 64 has circumference W1, and larger diameter D2 has circumference W2. Surface 44 is visible in FIG. 2b inside a flared portion resulting from rolling portion 70 of FIG. 2a into tube 76.

Diameter D1 of tube 76 of FIG. 2b is larger than the outer diameter d1 of elongated portion 12 of catheter 10, illustrated cut away in FIG. 2c to show inflation lumen 24. As also illustrated in FIG. 2c, an inflation aperture 80 is preformed through the side of elongated portion 12 into inflation lumen 24. Inflation aperture 80 in the final assembled form will become part of inflation aperture 46 (FIG. 1c).

FIG. 2d illustrates the insertion of the distal end of elongated portion 12 through tube 76. Tube 76 and elongated portion 12 are positioned so that aperture 80 adjoins the membrane of tube 76, and an attachment is made along a region defined by dotted line 82, with the region of attachment surrounding aperture 80. The attachment may be made in any known manner, as by use of fusion or adhesives. The attachment may be made with the aid of a mandrel, as described in conjunction with FIG. 7. When attachment in region 82 is complete, the end of tube 76 corresponding to opposite end 63 of FIG. 2a is folded back on itself or involuted in the direction indicated in FIG. 2d by arrows 84. FIG. 2e illustrates partial completion of the folding back. Because of the relatively limited compliance of polyethylene terephthalate, diameter D2 cannot be increased very much, as a highly compliant or elastic membrane might.

Folding back continues, pulling end 63 in the direction of arrows 88 of FIG. 2e. The flare in the membrane adjacent distal end 62 is lapped over end 63 and joined along a circular seam 94, to form the structure illustrated in FIG. 2f and also in FIG. 1.

The aperture through the membrane 32 of the balloon adjacent inflation aperture 80 (FIG. 2c) may be made after the joining along region 82 of elongated portion 12 and tube 76 (FIG. 2d). Alternatively, pressure may be applied by way of a valve 90 from a tank 92 of compressed gas through inflation lumen 24 as suggested by FIG. 2g, simultaneously stressing the attachment at region 82 for reliability test purposes, and rupturing the balloon membrane overlying aperture 80 to thereby define inflation aperture 46 of FIG. 1c.

FIG. 3 is a cross-sectional axial view of the distal end of a balloon catheter 210 according to another embodiment of the invention. In FIG. 3, elements corresponding to those of FIGS. 1 or 2 are designated by the same reference numbers in the 200 series. A balloon 230 includes a membrane 232 defining an inflatable portion 234 and an open channel 240 centered on longitudinal axis 208. The elongated portion 212 of catheter 210 includes a distal lumen 218 and an inflation lumen 224. Elongated portion 212 extends through the inflatable portion of the balloon rather than through the open channel, as in the embodiment of FIGS. 1 and 2. An inflation aperture 246 is defined through the side of elongated portion 212 into inflation lumen 224.

FIG. 4 illustrates steps of a method for making the catheter of FIG. 3. Elements of FIG. 4 corresponding to those of FIG. 2 are designated by the same reference numerals in the 200 series. In FIG. 4a, sheet 260 is similar to sheet 60 of FIG. 2a, except for the inclusion of two sets of aperture pairs 310 and 312, and the inclusion of additional tab sets 314, 316. Each aperture 310, 312 is in the form of a semicircle, with the flat portion of the semicircle lying along dotted lines 290 and 292, which corresponding in location to tapered sides 90 and 92, respectively, of FIG. 2. Tabs 314a and 314b ("314") and 316a and 316b ("316") extend generally outwardly from dotted lines 290 and 292.

Figure 4A:
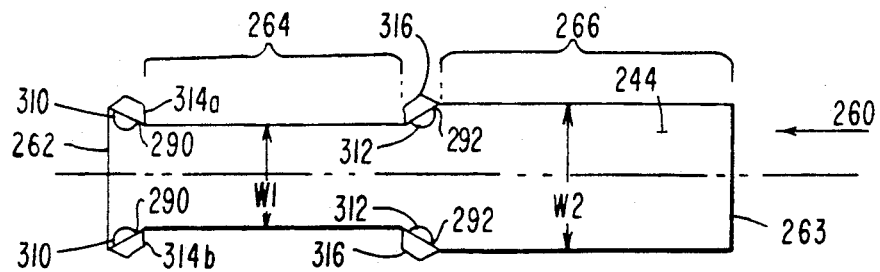
FIGS. 4a-4g, referred to jointly as FIG. 4, represent steps in the fabrication of a catheter similar to that of FIG. 3.
Figure 4B:
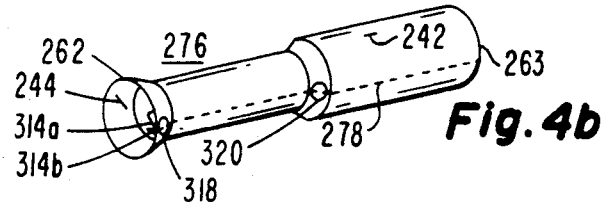
Figure 4C:
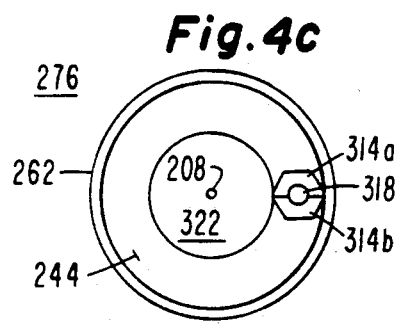

FIG. 4b illustrates the result of the rolling of membrane 260 into a tube 276 with a seam 278. The semicircular apertures 310 of FIG. 4a are joined together along then flat sides to form a circular aperture 318 centered on the seam, and semicircular apertures 312 are similarly joined to form a circular aperture 320. Tabs 316 are located inside tube 276 and are not visible in FIG. 4b, but portions of tabs 314a and 314b are visible. FIG. 4c is an axial view of the left end of the structure of FIG. 4b, illustrating central hole 322 through tube 276.

Figure 4D:
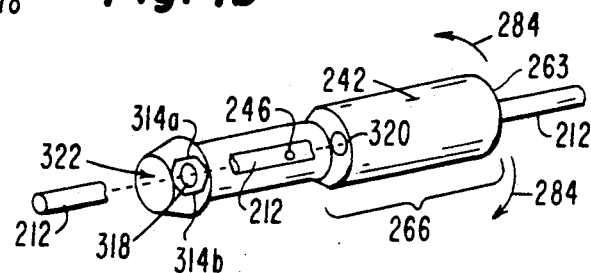
Figure 4E:
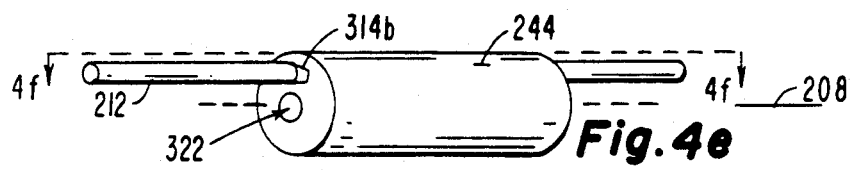
Figure 4F:
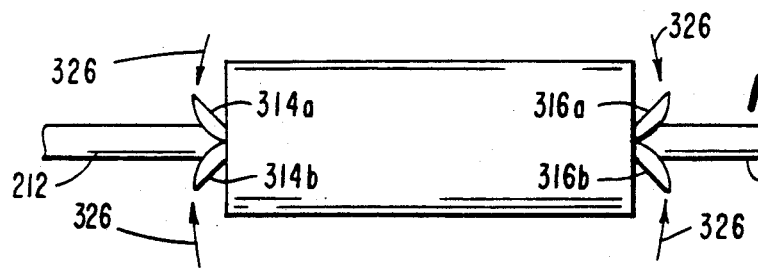
Figure 4G:
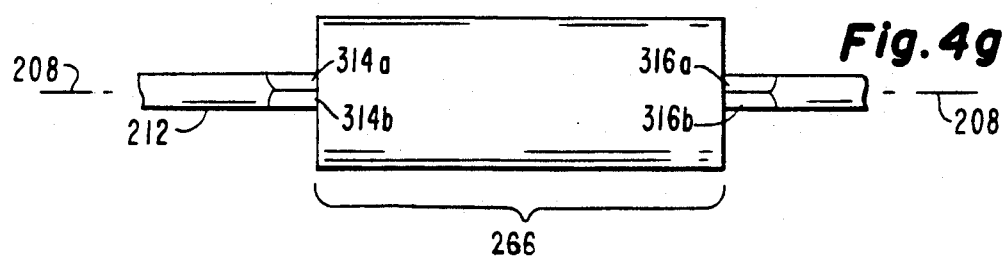

FIG. 4d illustrates tube 276 with the flared portion adjacent to end 262 pushed toward the right, and showing elongated portion 212 extending through circular apertures 318 and 320, with inflation aperture 246 therebetween. The larger end of tube 276 is involuted as described in conjunction with FIG. 2 by motion in the direction of arrows 284, to form the structure of FIG. 4e. FIG. 4f illustrates the structure of FIG. 4e looking in the direction of lines 4f-4f. Tabs 314a, 314b, 316a and 316b are pushed in the directions of arrows 326, toward the outer surface of elongated portion 212, and attached thereto as illustrated in FIG. 4g to form a sturdy connection.

It should be noted that the shape of apertures 310 and 312 will depend to a certain extent upon the compliance or elasticity of the balloon membrane, and less compliant materials may require that the flat side be somewhat curved to fit smoothly around elongated portion 12 without excessive bunching.

FIG. 5 illustrates another embodiment of the invention. In FIG. 5, elements corresponding to those of FIG. 1 are designated by the same reference numeral in the 400 series. In FIG. 5, catheter 410 has its balloon 430 attached near distal end 414 of elongated portion 412. The open end of distal lumen 418 is visible. As is more evident in axial end view in FIG. 5b, balloon 430 in its inflated form defines two distinct lobes 510 and 520, as a result of attachment of the balloon's membrane 432 to elongated portion 412. The attachment is along spaced elongated regions 522 and 524, seen generally in FIG. 5a. The attachment is illustrated in the longitudinal cross-section of FIG. 5d, looking in the direction of arrows 5d-5d of FIG. 5b. As illustrated in FIG. 5d, balloon 430 is made fluid-tight by gathering the balloon membrane 432 about, and fastening the gathered membrane to, the outer surface of elongated portion 412 near regions 526 at the distal and proximal ends of the balloon. In FIG. 5d, an inflation aperture 446 extends through the side of elongated portion 412 and opens into inflation lumen 424. Thus, aperture 446 opens from inflation lumen 424 into lobe 510 of the balloon. The other lobe, 520 (not illustrated in FIG. 5d), may be inflated through corresponding inflation aperture (not illustrated). Alternatively, single inflation aperture 446 may be used, while providing communication between lobes 510 and 520 by way of the space between balloon membrane 432 and the outer surface of elongated portion 412, as near regions 530 lying between attachment regions 522, and regions 532 lying between attachment regions 524.

Figure 5A:
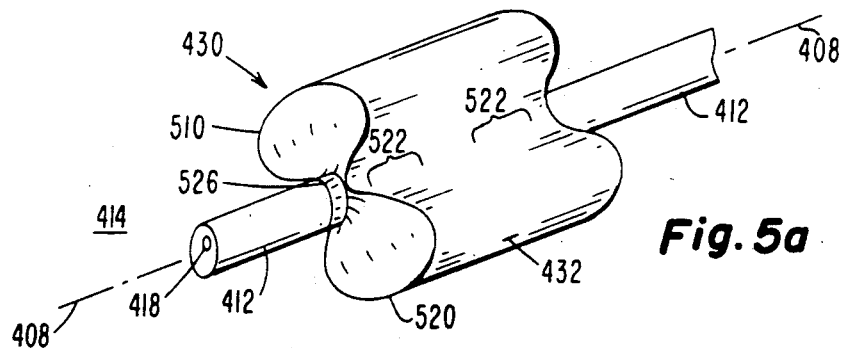
FIG. 5a is a perspective or isometric view of a dilatation catheter with a multi lobed inflated balloon.
Figure 5B:
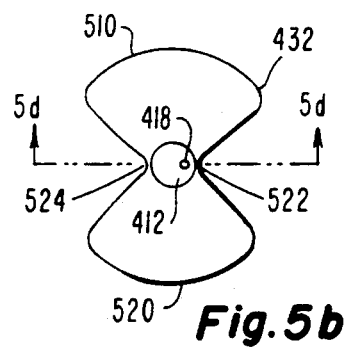
FIG. 5b is an end view of the balloon.
Figure 5C:
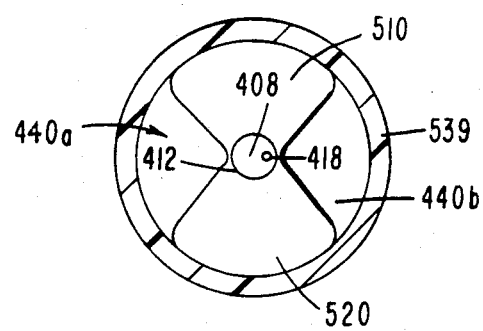
FIG. 5c is an axial cross-sectional view of a coronary artery and inflated multi-lobed balloon.
Figure 5D:
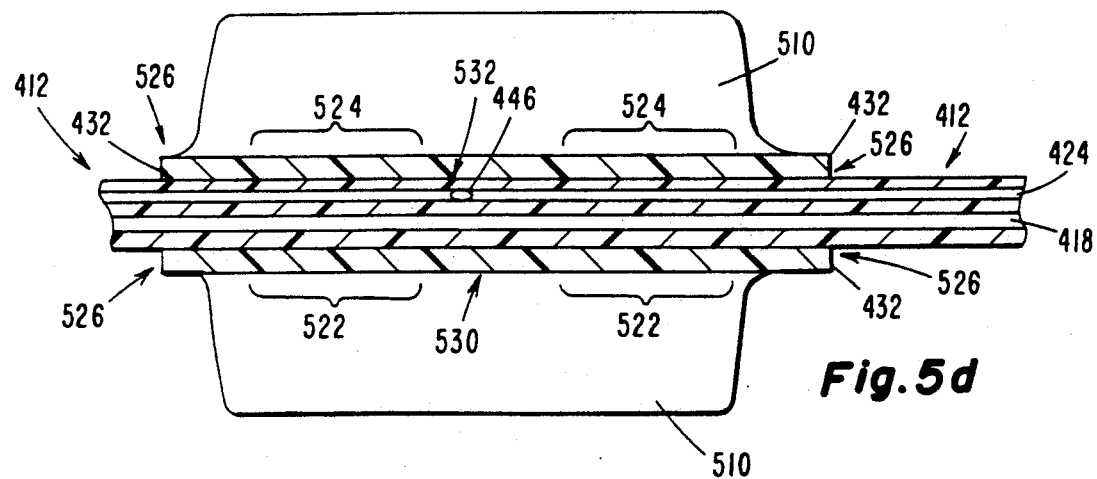
FIG. 5d is a longitudinal cross-section of the balloon illustrating its attachment to the catheter.

5c illustrates balloon 430 of catheter 410 of FIGS. 5a, 5b and 5d inflated within a vas defined by a circumferential wall, seen in cross-section as 539. As illustrated, a pair of open channels 440a, 440b lying between balloon lobes 510 and 520 allow the flow of body fluids axially along the vas. It should be noted that the term "axial" relates to idealized conditions such as those illustrated. Where flexible members are involved, they may assume arbitrary shapes, such as the shape of elongated portion 12 in FIGS. 1a and 1b, whereupon "axial" must be interpreted as relating to a portion of the axis, such as axis 8, 208, or 408, which is near the region in question.

The selection of the balloon membrane material is based upon a consideration relating to the novel structure, and upon considerations such as those appearing in articles discussing the inflated diameters of balloons for coronary angioplasty such as the article "Effect Of Inflation Pressures On Coronary Angioplasty Balloons," by Jain et al. printed at pages 26-28 of the Jan. 1, 1986 issue of The American Journal of Cardiology. As described therein, less compliant materials provide more constant inflated diameters over a range of pressures. Referring to the axial views of FIGS. 1b, 3 and 5c, one may consider what might occur to the cross-sections of channels 40, 240 and 440a and 440b, respectively, as the balloon inflation pressure is increased from a barely inflated condition. A totally elastic or high compliance balloon membrane material would expand at any location not restrained by the walls of a surrounding vas. The membrane material adjacent an open channel is not constrained, and such highly elastic membrane would tend to expand, thereby closing off the channel. Thus, a highly elastic material might provide an open channel at low inflation pressures, but would close off the channel at higher pressures. For this reason, a relatively low compliance material may be desirable for angioplasty, although a high-compliance material might be desirable for such purposes as controllably occluding a vas. A relatively low compliance material available for use in balloon catheters is polyethylene terephthalate. Conceptually, a low-compliance material used in a structure such as that described might be termed a "bag" rather than a "balloon", but the "balloon" terminology is well established and is accepted.

FIG. 6 illustrates steps in a process for making the balloon catheter of FIG. 5. In FIG. 6, elements corresponding to those of FIG. 5 are designated by the same reference numerals. FIG. 6a illustrates a formed sheet 660 of balloon membrane. Sheet 660 includes a central wide portion 666 having width W2 and first and second end portions 664 and 665 having width W1. Tapered regions 668 and 670 include slanted edges 690 and 692, respectively. FIG. 6b illustrates sheet 660 of balloon membrane 432 rolled into a tube 676 around elongated portion 412, and sealed along a seam 678. Tube 676 has a diameter in region 666 greater than the diameter of elongated portion 412, namely a diameter defined by circumferential dimension W2. The smaller diameter of tube 67b in end regions 664 and 665 is defined by circumferential dimension W1, selected to fit closely about the outer surface of elongated portion 412. End portions 664 and 665 are sealed to the outer surface of elongated portion 412 to form a closed balloon.

Figure 6A:
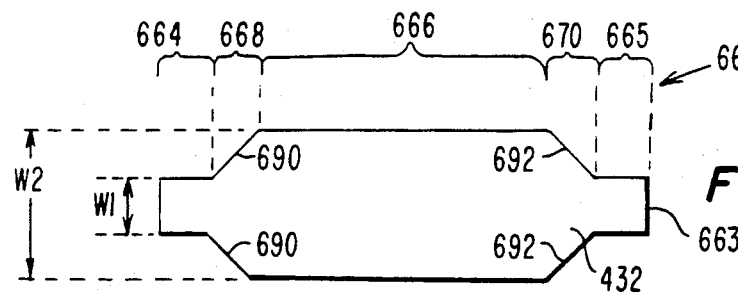
FIGS. 6a-6d, referred to jointly as FIG. 6, illustrate steps in the fabrication of a multi-lobed balloon catheter similar to that of FIG. 5.
Figure 6B:
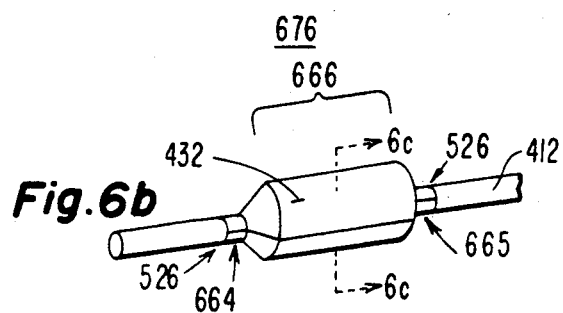
Figure 6C:
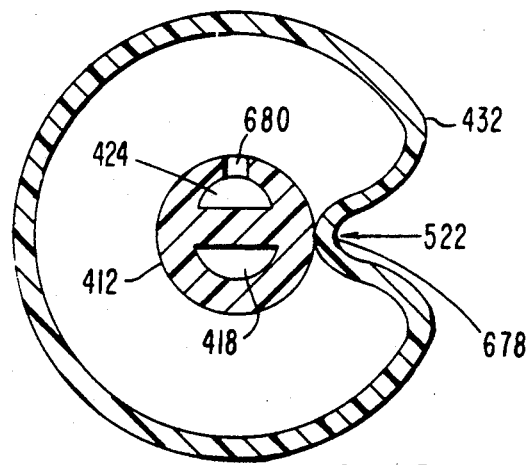

FIG. 6c illustrates a cross-section of the structure of FIG. 6b looking in the direction of arrows 6c-6c. In FIG. 6c, the distal lumen and the inflation lumen of elongated portion 412 are visible. Also visible in FIG. 6c is an inflation aperture 680, extending through the side of elongated portion 412 and into inflation lumen 424.

Figure 6D:
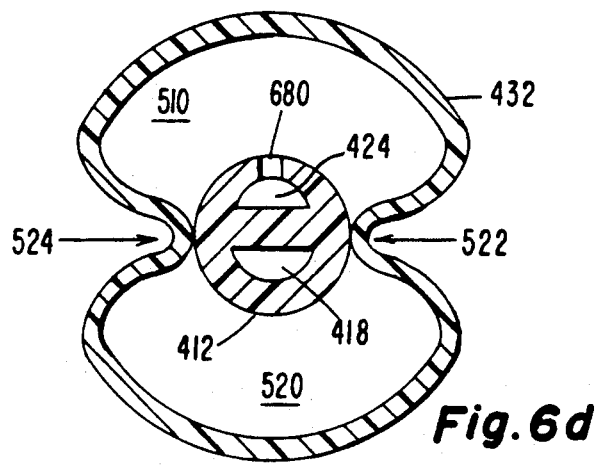

In FIG. 6c, the loose balloon membrane 432 along seam 678 is affixed to the outer surface of elongated portion 412 at longitudinally spaced locations 522 rotationally removed from inflation aperture 680. With this attachment, a balloon according to the invention is complete, as the balloon has a single lobe defining (in conjunction with a vas, not illustrated) a longitudinal channel about region 522. However, more axial blood flow in the context of an angioplasty catheter may be achieved by making a second attachment of loose balloon material 432 along an attachment line 524, as illustrated in FIG. 6d. With this attachment, the appearance of the cross-section of the inflated balloon is generally of a "figure-eight."

FIG. 7 illustrates an arrangement for making a balloon catheter with two parallel channels for the flow of body fluid. In FIG. 7, elements corresponding to those of FIG. 2 are designated by the same reference numbers in the 700 series. FIG. 7a illustrates a sheet 760 of balloon material formed in a manner similar to that of FIG. 2a. FIG. 7b illustrates sheet 760 formed into a tube 776 by a seam 778. Elongated portion 712 of a catheter is placed in a slot 798 of a cylindrical mandrel 796, dimensioned smaller than the smallest diameter of tube 776. FIG. 7d is an axial cross-section of elongated portion 712 and mandrel 796. FIG. 7e is a similar axial cross-section of a portion of the mandrel and elongated portion, with the mandrel and elongated portion inserted into tube 776, viewed in the region of the small diameter of the tube. An attachment is made between balloon membrane 732 and the outer surface of elongated portion 712 along an axially extending region 782 (FIG. 7f) with force exerted in the direction of an arrow 794. The attachment region surrounds inflation aperture 780. FIG. 7f illustrates the result of the withdrawal of mandrel 796. Inflation aperture 780 may be opened at this juncture. In FIG. 7g, attachment region 782 is placed against a support surface 799. FIG. 7g illustrates the application of force in the direction of an arrow 797 to form a second attachment region 782' between balloon membrane 732 and the outer surface of elongated portion 712, thereby defining two open channels 740a, 740b. Finally, the balloon is closed by drawing end 763 of tube 776 toward portion 762 as suggested by arrows 784 in FIG. 7h, and making a connection as described generally in conjunction with FIGS. 2e and 2f. FIG. 7i illustrates in axial view the inflated balloon 730 formed by the steps of FIGS. 7a-7h.

FIG. 9 illustrates alternative steps for fabrication of a balloon catheter. In FIG. 9, elements corresponding to those of FIG. 2 are designated by the same reference numerals. FIG. 9b illustrates in perspective or isometric view the distal end of elongated portion 12 of catheter 10, corresponding to the structure described in conjunction with FIG. 9a, with a portion of the distal end of elongated portion 12 cut away by a cut through its central axis (not separately shown) midway between distal lumen 1B and inflation lumen 24, and an intersecting cut transversely through inflation lumen 24 at a location 912, to define a surface 910, and to cause inflation lumen 24 to open at location 912, which is removed from the most distal part of elongated portion 12.

Figure 9A:
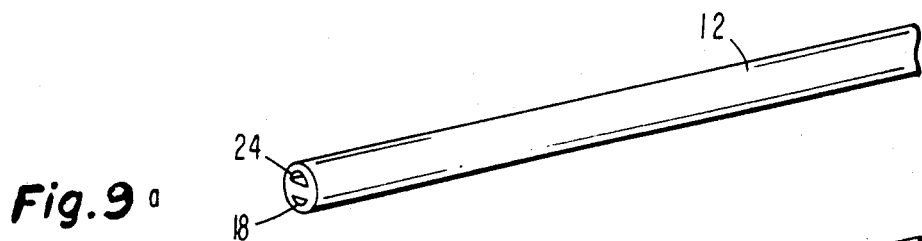
FIGS. 9a–9g, referred to jointly as FIG. 9, illustrate steps in the fabrication of a balloon catheter according to another embodiment of the invention.
Figure 9B:
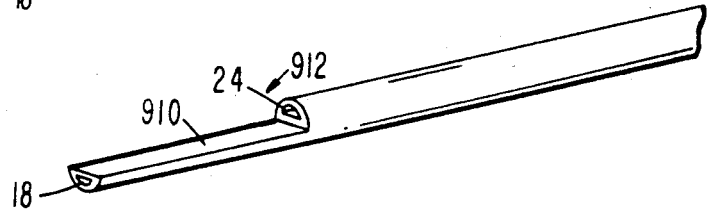
Figure 9C:
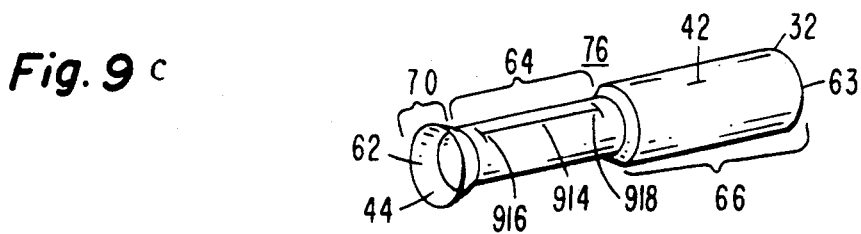
Figure 9E:
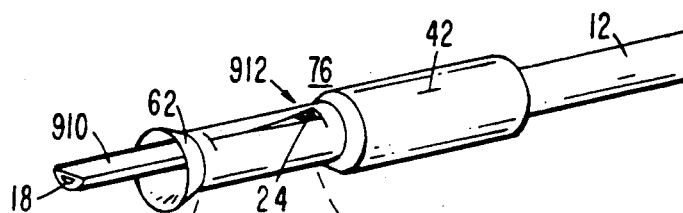
Figure 9D:
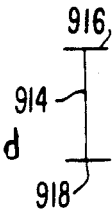
Figure 9G:
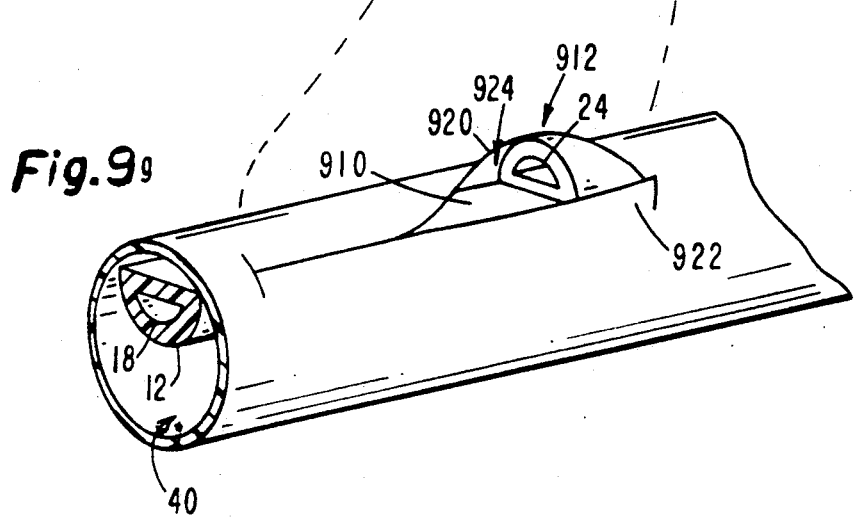
Figure 9F:
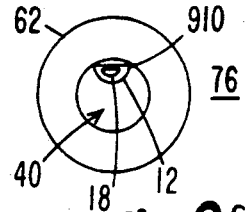

FIG. 9c illustrates a cylinder or tube 76 of balloon material, corresponding to the structure illustrated in FIG. 2b. Cylinder 76 of balloon material may be formed by rolling from a flat sheet as described in conjunction with FIGS. 2a and 2b. or may be formed by extrusion or by molding. A longitudinal slit illustrated as 914 is made through balloon membrane 32 in region 64 of tube 76. Additional slits, such as 916 and 918, may also be made, to aid the balloon membrane in conforming to the shape of the elongated portion 12 of catheter 10, as described below. FIG. 9d is a developed elevation view of longitudinal slit 914 and additional transverse slits 916 and 918. FIG. 9e is a perspective or isometric view of tube 76, with elongated portion 12 extending therethrough, corresponding to the step described in conjunction with FIG. 2d. In FIGS. 9e, elongated portion 12 is oriented with its cut surface 910 parallel to the surface of tube 76. FIG. 9f is an end view of the structure of FIG. 9e, looking from the distal end of the catheter. The flexibility of balloon material 32 allows flaps 920 and 922 of balloon material, defined by slits 914, 916 and 918, to move and conform themselves to the local surface of elongated portion 12, thereby opening an aperture in balloon membrane 32 which is illustrated as 924 in FIG. 9g, which is a close-up view of the slit region of the structure of FIG. 9e. The inner surface of tube 76 is bonded to flat surface 910, and to an adjacent portion of the curved surface of elongated portion 12. When the bonding is complete, any excess or unbonded portions of tabs 920 or 924 may be removed, if desired. The bonded structure as illustrated in FIGS. 9e, f and g corresponds to the bonded structure illustrated in FIG. 2d, with aperture 924 of FIG. 9 corresponding to the aperture through membrane 32 over inflation aperture 80, discussed in connection with FIG. 2d. This completes the steps of the alternative method, and fabrication of the catheter is completed by following folding and bonding steps corresponding to those of FIGS. 2e and 2f. Although the fabrication method of FIG. 9 is described in the context of an alternative to a part of process described in FIG. 2, it is equally applicable as an alternative to part of the process of FIG. 7. When used as an alternative to the process of FIG. 7, the step illustrated in FIGS. 9e, f and g precedes the step described in conjunction with FIG. 7g.

The step illustrated in FIG. 9b may also be used in conjunction with the method illustrated in FIG. 4, as an alternative to defining inflation aperture 246, so long as location 912 at which the inflation lumen opens (FIG. 9b) is located between apertures 318 and 320 of FIG. 4d, as for example at the location illustrated for inflation aperture 246. The salient advantage of a catheter made according to the method of FIG. 9 is that the most distal end of the catheter has a smaller diameter than the methods of FIGS. 2, 4 or 7, which may be advantageous for some coronary angioplasty because the small size allows access to smaller arteries, but it may be more flexible and harder to push through sclerotic deposits in other cases.

The alternative fabrication method described in conjunction with FIG. 9b may also be used in conjunction with the fabrication method described in conjunction with FIG. 6, as an alternative to the step of forming inflation aperture 680, and when so used provides the same advantage of smaller size and disadvantage of flexibility.

Figure 8:
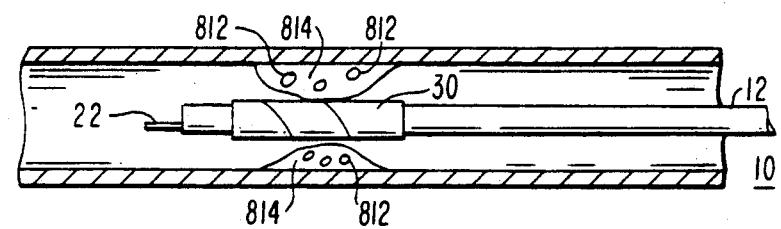
FIGS. 8a-8c, referred to jointly as FIG. 8, illustrate steps in the use of the catheters of FIGS. 1, 3 or 5.
Figure 8:
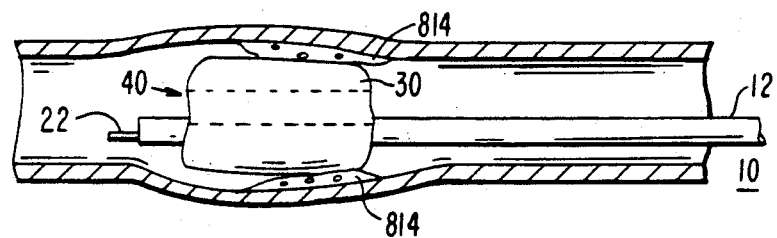
Figure 8:
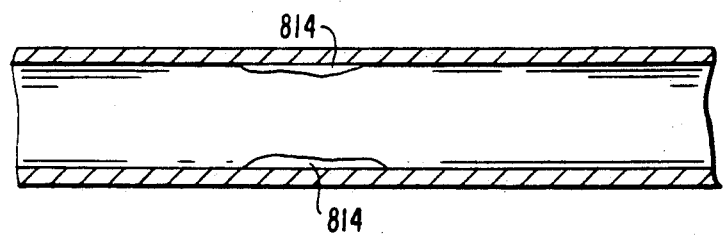

FIG. 8 illustrates steps in the use of a catheter formed according to the invention for angioplasty. In FIG. 8a, catheter 10 with balloon 30 deflated is inserted into the stenotic lumen of a coronary artery designated generally as 810. Small circles 812 in plaque 814 represent interstices resulting from uneven deposition of fatty plaque. FIG. 8b represents the result of applying inflation pressure to balloon 30 by way of the inflation lumen of catheter 10. As illustrated, the outermost portions of inflated balloon 30 press against the plaque deposits 812, tending to compress the deposits by squeezing the interstices. If desired, and if the catheter is properly equipped, microwave or radio-frequency energy may be applied at this stage of treatment as described in the aforementioned Rosen and Walinsky patent. Further, the diameter of the lumen may be measured during the procedure in accordance with the methods described in U.S. patent application Ser. No. 07/269,960 filed Nov. 10, 1988 in the names of Rosen and Walinsky. Averaged over a number of procedures, the inflated condition illustrated in FIG. 8b, in which open channel 40 allows blood to flow more or less freely through the artery, may be maintained without chest pain for a longer period of time than could the prior art nonperfusing balloon catheters which totally occluded the artery. The longer period of time is believed to correlate with improved result. FIG. 8c illustrates artery 810 after the desired time has elapsed or the desired result achieved and the catheter has been withdrawn.

Other embodiments of the invention will be apparent to those skilled in the art. For example, the seam 94 in balloon 30 of FIG. 1 may be at any location, even toward the inside of the torus, and may lap in either direction, or may even be butted if a sufficiently strong joint can be made, as by reinforcement. The catheter may be equipped with conventional devices such as fiber-optic cables for viewing or laser purposes. Microwave or radio-frequency cables may also be used in conjunction therewith for heating, and antenna elements may be printed on the balloon membrane. Multiple balloons having different inflated diameters may be located at different longitudinal positions along the catheter. If these balloons are of the lobed type described in conjunction with FIGS. 5 and 6, the rotational position of the lobes around the axis may be varied. The structures may be made by methods other than those described, as for example for certain materials the structure of FIG. 3 may be made by heating an inflated balloon membrane and thrusting a heated elongated portion therethrough. Instead of starting with sheet balloon material and rolling to form cylinders of balloon material as described in conjunction with FIGS. 2, 4, 6 and 7, molded or extruded cylinders of balloon membrane may be the starting point for the methods of fabrication.

What is claimed is:

1. A catheter, comprising:

an elongated portion defining proximal and distal ends and also defining at least one elongated lumen adapted for the flow of fluid therethrough;

balloon membrane means coupled near said distal end of said elongated portion, said balloon membrane means including an exterior surface, said balloon membrane means being adapted for inflation within a vas and being configured, when so inflated within a vas, to define a toroidal balloon including a central opening adjacent said exterior surface of said balloon membrane means, said central opening extending from a distal end of said balloon to a proximal end of said balloon, said central opening being larger in diameter than said elongated portion, said elongated portion passing through said central opening and being affixed to said exterior of said balloon membrane means of said central opening to thereby define an aperture for the flow of fluids therethrough from said proximal to said distal ends of said balloon membrane means; and at least one aperture between said elongated lumen defined by said elongated portion and the interior of said balloon.

2. A method for making a balloon catheter, said method comprising the steps of:

forming an elongated cylindrical membrane defining an axis, at least one inner diameter in a plane perpendicular to said axis, a length parallel to said axis, and open first and second ends;

inserting through said open first end of said cylindrical membrane, in a direction about parallel with said axis, an elongated portion of said catheter defining an axial lumen adapted for the flow of inflation fluid therethrough, said elongated portion having an overall outer diameter smaller than said inner diameter of said cylindrical membrane;

attaching a portion of said inner wall of said cylindrical membrane to the exterior of said elongated portion of said catheter near a distal end of said elongated portion of said catheter, said attachment being performed at least at locations along a line approximately parallel with said axis;

opening said lumen to the exterior of said elongated portion of said catheter at a location which when said balloon catheter is made lies between first and second ends of said balloon; and after said attaching step, closing said open first and second ends in such a manner as to cause said membrane to form a toroidal balloon defining a central opening having said inner diameter, through which central opening said elongated portion passes, to thereby leave a portion of said central opening free for passage of body fluids therethrough.

3. A method according to claim 2 wherein said step of open said lumen is performed before said step of closing.

4. A method according to claim 3 wherein said step of opening said lumen comprises:

an initial step preceding said step of inserting, said initial step including the steps of defining an aperture in the side of said elongated portion of said catheter, said aperture extending into said axial lumen; and wherein said step of attaching includes the step of positioning said balloon membrane over said aperture in said elongated portion of said catheter.

5. A method according to claim 2 wherein said step of closing includes the step of pulling said balloon membrane at said first and second ends of said cylindrical membrane relatively toward each other exteriorly of the cylinder of said cylindrical membrane; and attaching the periphery of said first open end to the periphery of said second open end to thereby close said first and second ends on each other to form said balloon and thereby define, when said balloon is inflated, a toroidal shape.

6. A method for making a balloon catheter, comprising the steps of:

forming an elongated cylindrical membrane including a right circular portion defining a central opening and at least one flared portion, said cylindrical membrane defining a first open end and also a second open end adjacent the large end of said flared portion, with said central opening extending between said first and second open ends;

defining an aperture through said flared portion of said balloon membrane;

inserting through said aperture the distal end of an elongated portion of said catheter defining a lumen adapted for the flow of fluid therethrough;

sealing the periphery of said aperture to the exterior surface of said elongated portion; and closing said first and second open ends in such a manner as to cause said membrane to form a toroidal balloon with said central opening extending parallel with said elongated portion.

* * * * *